United States Patent
Arav et al.

(10) Patent No.: US 8,580,487 B2
(45) Date of Patent: *Nov. 12, 2013

(54) METHODS OF PRESERVING FUNCTIONALITY OF AN ORGAN, PRESERVING FERTILITY OF A PATIENT UNDERGOING A TREATMENT EXPECTED TO CAUSE STERILITY AND ASSURING A SUPPLY OF VIABLE GAMETES FOR FUTURE USE

(75) Inventors: Amir Arav, Tel Aviv (IL); Yehudit Natan, Holon (IL); Saar Yavin, Netanyah (IL); Uri Meir, Kibbutz Bet Hashita (IL); Udi Damari, Ganiey Tikva (IL)

(73) Assignee: Core Dynamics Limited, Hamilton (BM)

( * ) Notice: Subject to any disclaimer, the term of this patent is extended or adjusted under 35 U.S.C. 154(b) by 843 days.

This patent is subject to a terminal disclaimer.

(21) Appl. No.: 11/102,728

(22) Filed: Apr. 11, 2005

(65) Prior Publication Data

US 2005/0175975 A1 Aug. 11, 2005

Related U.S. Application Data

(63) Continuation of application No. 10/155,648, filed on May 28, 2002, now Pat. No. 6,916,602.

(60) Provisional application No. 60/293,549, filed on May 29, 2001.

(51) Int. Cl.
*A01N 1/02* (2006.01)

(52) U.S. Cl.
USPC ............................. 435/1.2; 435/1.1; 435/1.3

(58) Field of Classification Search
USPC .............................................. 435/1.1, 1.2, 1.3
See application file for complete search history.

(56) References Cited

U.S. PATENT DOCUMENTS

| | | | |
|---|---|---|---|
| 5,217,860 A | 6/1993 | Fahy et al. | |
| 5,873,254 A | 2/1999 | Arav | |
| 6,187,529 B1 | 2/2001 | Fahy et al. | |
| 6,916,602 B2 * | 7/2005 | Arav | 435/1.3 |
| 2002/0064768 A1 | 5/2002 | Polyak et al. | |

FOREIGN PATENT DOCUMENTS

| | | |
|---|---|---|
| EP | 0 096 997 A1 | 12/1983 |
| EP | 0 664 080 A1 | 7/1995 |
| WO | 91/06135 | 2/1991 |
| WO | WO 91/01635 | 2/1991 |
| WO | 91/07085 | 5/1991 |
| WO | WO 91/07085 | 5/1991 |
| WO | 91/10361 A1 | 7/1991 |

OTHER PUBLICATIONS

Yin et al., "Transplantation of intact rat gonads using vascular anastomosis: effects of cryopreservation, ischaemia and genotype", Human Reproduction 18 (6) : 1165-1172 (2003).*
Arav et al., "Whole sheep ovary cryopreservation and transplantation", Fertility and Sterility 82 (6) 1714-1715 (2004).*
Pascual et al., "Restoring the endothelium of cryopreserved arterial grafts: co-culture of venous and arterial endothelial cells", Cryobiology 49 : 272-285 (2004).*
Dietzman, R.H., et al., "Long term functional success following freezing of canine kidneys", *Surgery*, vol. 74, No. 2, pp. 181-189 (1973).
Guttman, P.M., et al., "Survival of Canine Kidneys After Treatment with Dimethyl-sulfoxide, Freezing at -80° C., and Thawing by Microwave Illumination", Cryobiology, vol. 14, pp. 559-567 (1977).
Karaw, A.M. Jr., "Problems of Organ Cryopreservation", *In Organ preservation for transplantation*, (ed. Karow, A.M. and Pegg, D.E.) pp. 517-552 (Marcel Dekker, New-York, US, 1981).
Abstract: Jacobsen, I.A., et al., "Effect of Cooling and Warming Rate on Glycerolized Rabbit Kidneys", *Cryobiology*, vol. 19, pp. 668 (1982).
Schmidt, W.D., "Survival of frogs in low temperature", *Science*, vol. 215, No. 5, pp. 6997-6998 (1982).
Storey, K.B., et al., "Hatchling turtles survive freezing during winter hibernation", *Proc. Natl. Acad. Sci. USA*, vol. 85, No. 21, pp. 8350-8354 (1988).

(Continued)

*Primary Examiner* — Jon P Weber
*Assistant Examiner* — Kara Johnson
(74) *Attorney, Agent, or Firm* — Nath, Goldberg & Meyer; Joshua B. Goldberg; Jerald L. Meyer

(57) ABSTRACT

A method of preserving functionality of an organ. The method includes removing a whole organ and associated vasculature, cryo-preserving the whole organ, allowing a period of time to elapse, thawing the whole organ including vasculature and introducing the whole organ into a recipient so that the organ is supplied with blood by vasculature belonging to the recipient. Further disclosed is a method of preserving fertility of a patient undergoing a treatment expected to cause sterility. The method include removing a whole gonadal organ from the patient, cryo-preserving the whole gonadal organ, conducting the treatment and waiting for an effect thereof to subside, thawing the whole gonadal organ and introducing the whole gonadal organ where it is supplied with blood by the vasculature system of the patient. Further disclosed is a method of assuring a supply of viable gametes for future use, the method includes removing a whole gonadal organ from a patient, cryo-preserving the whole gonadal organ, waiting until viable gametes are desired by the patient, thawing the organ and introducing the gonadal organ into the patient so that it is supplied with blood by a vasculature system belonging to the patient.

16 Claims, 4 Drawing Sheets

(56) References Cited

OTHER PUBLICATIONS

Storey, K.B., "Life in a frozen state: adaptive strategies for natural freeze tolerance in amphibians and reptiles", *Am. J. Physiol.*, vol. 258, R559-R568 (1990).
Wang, T. et al., "Freeing Preservation of the Mammalian Cardiac Explant V. Cryoprotection by Ethanol", *Cryobiology*, vol. 29, pp. 470-477 (1992).
Banker, M.C. et al., "Freezing Preservation of the Mammalian Cardiac Explant IV. Functional Recovery After 8-Hour Freezing", *Curr. Surg.*, vol. 48, pp. 428-430 (1991).
Rubinsky, B. et al., "Freezing of Mammalian Livers with Glycerol and Antifreeze Proteins", Biotech. Bioph. Res. Comm., vol. 200, No. 2, pp. 732-741 (1994).
Soltys, K.A. et al., "Successful Nonfreezing, Subzero Preservation of Rat Liver with 2,3-Butanediol and Type 1 Antifreeze Protein", *J. of Surgical Research*, vol. 96, No. 1, pp. 30-34, (2001).
Karlasson, J.O.M. et al., "Long-term storage of tissues by cryopreservation: critical issues", *Biomaterials*, vol. 17, pp. 251-272 (1977).
Mazur, P., "The Role of Intracellular Freezing in the Death of Cells Cooled at Supraoptimal Rates", *Cryobiology*, vol. 14, pp. 251-272 (1977).
Fuller, B.J., "Low temperature preservation in medicine and veterinary science", (ed. Grout B.W.W. & Morris G.J.) pp. 432-450 (Edward Arnold, London, GB, 1987).
Wang, T. et al., "Freezing Preservation of Adult Mammalian Heart at High Subzero Temperatures", *Cryobiology*, vol. 28, pp. 171-176 (1991).
Fahy, G.M. et al. "Vitrification as an Approach to Cryopreservation" *Cryobiology*, vol. 21, pp. 407-426 (1984).
Kheirabadi, B.S. et al, "Permanent Life Support by Kidneys Perfused with a Vitrifiable (7.5 Molar) Cryoprotectant Solution", *Transplantation*, vol. 70, No. 1, pp. 51-57 (2000).
Steponkus, P.L. et al., "Cryopreservation of *Drosophila melanogaster* embryos", *Nature*, vol. 345, pp. 170-172 (1990).
Mazur, P. et al., "Cryobiology Preservation of *Drosophila melanogaster* embryos", *Science*, vol. 258, pp. 1932-1935 (1992).
Armitage, W.J. et al., "The Influence of Cooling Rate on Survival of Frozen Cells Differs in Monolayers and in Suspensions", *Cryoletters*, vol. 17, pp. 213-218 (1996).
Koebe, H.G. et al., "Temperature Gradients in Freezing Chambers of Rate Controlled Cooling Machines", *Cryobiology*, vol. 30, pp. 349-352 (1993).
Byrne, J. et al., "Effects of Treatment on Fertility in Long-Term Survivors of Childhood Adolescent Cancer", *N. Engl. J. Med.*, vol. 317, No. 21, pp. 1315-1321.
Ataya, K. et .al., "Chemotherapy-induced Premature Ovarian Failure: Mechanisms and Prevention", *Steroids*, vol. 54, pp. 607-626 (1989).
Familiari, G. et al., "Ultrastructure of human ovarian primordial follicles after combination chemotherapy for Hodkin's disease", *Hum. Reprod.*, vol. 8, No. 12, pp. 2080-2087 (1993).
Arav, A. et al., "Phase Transition Temperature and Chilling Sensitivity of Bovine Oocytes", *Cryobiology*, vol. 33, pp. 589-599 (1996).
Zeron, Y. et al., "Kinetic and Temporal Factors Influence Chilling Injury to Germinal Vesicle and Mature Bovine Oocytes", *Cryobiology*, vol. 38, pp. 35-42.
Zenzes, M.T. et al., "Effects of chilling to 0° C. on the morphology of meiotic spindles in human metaphase II oocytes", *Fertil. Steril.*, vol. 75, No. 4, pp. 769-777, (2001).
Hovatta, O. et al., "Cryopreservation of human ovarian tissue using dimethylsulphoxide and propandiol-sucrose as cryoprotectants", *Hum. Reprod.*, vol. 11, No. 7, pp. 1487-1491 (1996).
Newton, H. et al., "Low temperature storage and grafting of human ovarian tissue", *Hum. Reprod.*, vol. 11, No. 7, pp. 1487-1491 (1996).
Gosden, R.G. et al., "Low temperature storage and grafting of human ovarian, tissue", *Mol. Cell Endocrinol.*, vol. 163, pp. 125-129 (2000).
Gosden, R.G. et al., "Restoration of fertility to oophorectomized sheep by ovarian autografts stored at -196° C.", Hum. Reprod., vol. 9, No. 4, pp. 597-603.
Baird, D.T. et al., "Long-Term Ovarian Function in Sheep after Ovariectomy and Transplantation of Autografts Stored at -196°C", *Endocrinology*, vol. 140, No. 1, pp. 462-471 (1999).
Kim, S.S. et al., "The future human ovarian cryopreservation and transplantation: fertility and beyond", *Fert. and Sterl.*, vol. 75, No. 6, pp. 1049-1056 (2001).
Siebzehnrubl, E. et al., "Freezing of human ovarian tissue—not the oocytes the granulose is the problem", *Mol. Cell. Endicrinol.*, vol. 169, pp. 109-111 (2000).
Radford, J.A. et al., "Orthotopic reimplantation of cryopreserved ovarian cortical strips after high-dose chemotherapy for Hodgkin's lymphoma", *Lancet*, vol. 357, pp. 1172-1175 (2001).
Hillier, S.G., "The Parkes Lecture: Controlled ovarian stimulation in women", J. *Reprod. and Fert.*, vol. 120, pp. 201-210 (2000).
Aubard, Y. et al., "Greffes et Transplantations Ovariennes Chez la Femme: le Point", Revue Francaise de Gynecologie et d'Obstetrique, vol. 88, No. 12, pp. 583-590 (1993), abstract.
Salle, B. et al., "Normal pregnancies and live births after autograft of frozen-thawed hemi-ovaries into ewes", *Fert. and Sterl.*, vol. 77, No. 2, pp. 403-408 (2002), abstract.
Salle, B. et al., "Restoration of ovarian steroid secretion and histologic assessment after freezing, thawing, and autograft of a hemiovary in sheep", *Fert. and Sterl.*, vol. 72, No. 2, pp. 366-370, (1990).
Rubinsky, B. et al., "Freezing of Mammalian Livers with Glycerol and Antifreeze Proteins", *Biochem. and Biophys. Research Communications*, Academic Press Inc., vol. 200(2) pp. 732-741 (1994).
Pegg, "Problems in the Cryopreservation of Tissues and Organs", *Cryobiology* 33(6): 619 (1996).
Baust et al., "A Molecular Basis of Cryopreservation Failure and its Modulation to Improve Cell Survival", *Cell Transplantation* 10:561-571 (2001).
Candy et al., "Effect of Cryoprotectants on the Survival of Follicles in Frozen Mouse Ovaries", *Journal of Reproduction and Fertility* 110: 11-19 (1997).
Gunasena et al., "Live Births and Autologous Transplant of Cryopreserved Ovaries", *Human Reproduction* 12(1): 101-106 (1997).
Scott et al.., "Microsurgical Ovarian Transplantation in the Primate", *Fertility and Sterility* 36(4) (1981).
Eltabbakh et al., "Estrogen Replacement Therapy Following Oophorectomy in Women with a Family History of Ovarian Cancer", *Gynecologic Oncology* 66:103-107 (1997).
Denjean et al., "Ovarian Transplantation by Selective Microvascular Anastomoses in the Rabbit", *British Journal of Obstetrics and Gynaecology* 89:652-656 (1982).
Bedaiwy et al. "Cryopreservation of Intact Human Ovary With Its Vascular Pedicle", Human Reproduction, 21(12): 3258-3269, 2006.
Bedaiwy et al. "Restoration of Ovarian Function After Autotransplantation of Intact Frozen-Thawed Sheep Ovaries With Microvascular Anastomosis", Fertility and Sterility, 79(3): 594-602, Mar. 2003.
Courbiere et al. "Follicular Viability and Histological Assessment After Cryopreservation of Whole Sheep Ovaries With Vascualr Pedicle by Vitrification", Fertility and Sterility, 84(Suppl.2): 1065-1071, Oct. 2005.
Dittrich et al. "Cryopreservation of Complex Systems: Slow Freezing Has Not Had Its Day Yet", Rejuvenation Research, 10(1): 101-102, 2007.
Imhof et al. "Cryopreservation of a Whole Ovary as a Strategy for Restoring Ovarian Function", Journal of Assisted Reproduction and Genetics, 21(12): 459-465, Dec. 2004.
Imhof et al. "Orthotopic Microvascular Reanastomosis of Whole Cryopreserved Ovine Ovaries Resulting in Pregnancy and Live Birth", Fertility and Sterility, 85(Suppl.1): 1208-1215, Apr. 2006.
Martinez-Madrid et al. "Apoptosis and Ultrastructural Assessment After Cryopreservation of Whole Human Ovaries With Their Vascular Pedicle", Fertility and Sterility, 87(5): 1153-1165, May 2007.
Martinez-Madrid et al. "Freeze-Thawing Intact Human Ovary With Its Vascular Pedicle With a Passive Cooling Device", Fertility and Sterility, 82(5): 1390-1394, Nov. 2004.

(56) References Cited

OTHER PUBLICATIONS

Wang et al. "Fertility After Intact Ovary Transplantation. Frozen Banking of Whole Organs for Transplantation is Starting to Look Feasible", Nature, 415: 385, Jan. 24, 2002.
Yingbin "Yingbin-Nature (Guangdong) Wood Industry Co. versus International Trade Commission", U.S. Court of Appeals Federal Circuit, 534 F3d 1322, 87 USPQ2D 1590, No. 2007-1311, Decided Jul. 31, 2008.
Supplemental Response Dated Nov. 18, 2010 to Response of Nov. 12, 2010 to Official Action Dated May 11, 2010 From the US Patent and Trademark Office Re.: U.S. Appl. No. 11/102,728.
Marrinan et al. "Polycystic Ovarian Disease (Stein-Leventhal Syndrome)", Obstetrics/Gynecology, Medscape, 2010.

* cited by examiner

METHODS OF PRESERVING FUNCTIONALITY OF AN ORGAN, PRESERVING FERTILITY OF A PATIENT UNDERGOING A TREATMENT EXPECTED TO CAUSE STERILITY AND ASSURING A SUPPLY OF VIABLE GAMETES FOR FUTURE USE

This is a Continuation Application of U.S. patent application Ser. No. 10/155,648 filed May 28, 2002, now U.S. Pat. No. 6,916,602 issued on Jul. 12, 2005, which claims benefit of U.S. Patent Application No. 60/293,549 filed May 29, 2001, the entire contents of which are hereby incorporated by reference in its entirety.

FIELD AND BACKGROUND OF THE INVENTION

The present invention relates to methods of preserving functionality of an organ, preserving fertility of a patient undergoing a treatment expected to cause sterility and assuring a supply of viable gametes for future use and, more particularly, to a methods which rely upon removal of an organ, cryopreservation of the removed organ and reintroduction of the cryopreserved organ into a recipient in such a way that the vasculature of the recipient supplies blood to the introduced organ or a portion thereof.

Undoubtedly, successful cryopreservation of solid organs of clinical interest would have a significant impact on the field of organ transplantation. However, despite several decades of research freezing and thawing of solid organs remains largely impractical (Dietzman et al., 1973; Guttman et al., 1977; Pegg et al., 1987; Karow, 1981; Jacobsen et al., 1982).

Attempts to understand the mechanism by which cold-blooded animals survive freezing in nature (Storey and Storey, 1988; Storey, 1990) have led to successful, short-term cryopreservation of hearts and livers by freezing at high sub-zero temperatures (−3.4° C. to −4° C.), (Wang et al., 1992; Banker et al., 1991, Rubinsky et al., 1994, Soltys et al., 2001).

Cryopreservation at lower temperatures, which is necessary for long-term storage, was attempted in dog intestines, but vascular injury was observed after thawing (Karlasson et al., 1996). Livers have regained partial function after freezing to −60° C. (Mazur, 1977), dog spleens (Fuller, 1987) and ureters (Pegg, 1987) have survived deep freezing and transplantation, and kidneys have survived freezing to −80° C.

(Fahy et al., 1984) proposed vitrification (ice free cryopreservation) as an alternate strategy for for organ cryopresernation (Kheirabadi et al., 2000). Vitrification produced a high survival rate in cryopreserved small organisms such as *Drosophila* embryos at −196° C. (Steponkus et al., 1990; Mazur et al., 1992).

Thus, successful cryopreservation of organs apparently requires a specific optimal cooling rate, because damage may occur if organs are frozen either too rapidly or too slowly (Karlsson and Toner, 1996; Mazur, 1977). Cooling too slowly (<1° C./min) causes extracellular crystallization which may physically disrupt the vital tissue architecture (Fuller, 1987; Pegg, 1987), whereas at higher cooling rates intracellular crystallization will cause irreversible damage.

Further, cryopreservation of large-volume samples, such as tissues or organs, introduces heat transfer problems. In macroscopic samples there is a large thermal gradient from the surface of the sample to the interior. For example, it was shown that cells survived equally when frozen as isolated cells or in a monolayer, only when the applied cooling rate was less than 0.5° C./min. Moreover, the survival of cells in monolyer was higher than isolated cells using the determined optimal cooling rate of 0.2° C./min. This indicates that the attached cells were more tolerant of slow cooling injury (Armitage et al., 1996). The need for a slow cooling rate is further illustrated by the cooling rate at which a Wood frog survives freezing (less than 0.1° C./minute; Schmid, 1982).

Typically, prior art freezing techniques produce temperature gradients within the freezing chamber which make it difficult to achieve an optimal cooling rate (Koebe et al., 1993). In addition, cooling rates slower than 0.1° C./minutes are hard to control in a programmable freezing apparatus since the accuracy of the temperature measurement is within that range (OMEGA ENGINEERING, INC). U.S. Pat. No. 5,873,254 to Arav teaches a device capable of producing a uniform cooling rate of 0.1° C./min throughout a bilogical sample. However, the earlier teachings of Arav do not disclose methods for cryopreservation of whole organs and subsequent introduction of those whole organs into a recipient subject. Specifically, the earlier teachings of Arad do not include methods for thawing a whole organ without impairing functionality thereof and surgical techniques for anastomic transplantation.

It is well established that treatment of a malignant disease by radiotherapy or chemotherapy can have dramatic and irreversible effect, on fertility, especxially in female patients (Byrne et al., 1987; Ataya, 1989; Familiari, 1993).

Thus, there is a recognized need, but no established method, for cryopreservation of a gonadal organ for subsequent reimplantation for patients at risk for premature sterility as a result of planned cancer treatment. While oocyte cryopreservation theoretically offers a means of preserving fertility for these patients, severe practical problems for oocyte cryopreservation remain unsolved (Arav et al., 1996; Zeron et al., 1999; Zenzes et al., 2001). Similarly, while cryopreservation of semen for male patients is available, it is not an optimum method of assuring male sterility. Cryopreservation of oocytes and/or semen typically require laboratory intervention in the form of IVF procedures. This prospect is daunting to many patients for a variety of reasons including emotional and religious reasons. Thus, storage and later use of a gonadal organ for conception by conventional methods offers significant advantages over previously available alternatives.

A high proportion of viable follicles have been found to survive in human ovarian tissue after freeze-thawing (Hovatta et al., 1996; Newton et al., 1996; Oktay et al., 1997), and this has aroused interest in the procedure as a potential means of preserving the fecundity of patients at risk of premature ovarian failure (Donnez et al., 1998; Newton et al., 1998). However, freezing and thawing of the whole ovary was not reported.

Gosden and colleagues (1994) have achieved limited success in sheep using ovarian cortex freezing leading to speculation that this technique may be applicable to humans. The sheep ovary is similar to the human ovary in that it has a dense fibrous stroma and relatively high density of primordial follicles in the ovarian cortex.

Autotransplantation of frozen-banked and fresh ovarian cortex cryopreservation ovarian cortex, have resulted in two pregnancies (Gosden et al., 1994). Baird et al. (1999) performed frozen tissue autotransplantation in eight sheep, which were monitored for up to 22 months. All the animals resumed cyclicity and showed hormone production, however, it was established that there was a drastic reduction in the total follicular number, and the resumption of cyclical ovarian function was temporary. Thus, despite recent advances in this area; transplantation of a functional portion of an ovary for purposes of restoring full ovarian function remains unreliable. Therefore, freezing and grafting of human ovarian tissue is not considered clinical option (Kim et al., 2001).

Clinical acceptability of ovarian tissue transplantation will require higher numbers of follicles survive and retain the capability to develop and ovulate. Recently it has been demonstrated that during freezing of cortical ovarian slices granulosa cells are more damaged than oocytes (Siebzehnrubl et al., 2000).

Further, currently accepted experimentyal practice idictates use of ovarian slices resulting in schemic damage as a result of non-vascular transplantation. Still further, the need for an IVF procedure in addition to preparing tissue for cryopreservation is time consuming and increases costs of the procedure. Finally, in those cases where ovarian function has been restored, long post=implantation delays are observed (Radford et al., 2001).

Transplantation of whole ovary including vascular has been recognozied as a theoretical method of solving the problems described above. While Ovary transplantation has been known for decades, (Nobel Lecture, Dec. 11, 1912: "Suture of blood-vessels and transplantation of organs"), autotransplantation has been considered impractical because of the absence of long term organ cryopreservation.

There is thus a widely recognized need for, and it would be highly advantageous to have, methods of preserving functionality of an organ, methods of preserving fertility of a patient undergoing a treatment expected to cause sterility and methods of assuring a supply of viable gametes for future use devoid of the above limitation.

SUMMARY OF THE INVENTION

According to one aspect of the present invention there is provided a method of preserving functionality of an organ. The method includes: (a) removing at least a whole organ including vasculature from a donor; (b) cryo-preserving the whole organ including vasculature; (c) allowing a period of time to elapse; (d) thawing the whole organ including vasculature so that at least a portion of cells contained therein resume biological activity; and (e) introducing the whole organ including vasculature into a recipient so that a blood vessel present in the vasculature of the whole organ including vasculature is supplied with blood by a vasculature system belonging to the recipient. For purposes of this specification and the accompanying claims, the phrase "whole organ including vasculature" refers to those blood vessels responsible for local supply of blood to the removed organ.

According to another aspect of the present invention there is provided a method of preserving fertility of a patient undergoing a treatment expected to cause sterility, the method includes; (a) removing at least one whole gonadal organ including vasculature from the patient; (b) cryo-preserving the at least one whole gonadal organ including vasculature; (c) conducting the treatment and waiting for an effect thereof to subside; (d) thawing the at least one whole gonadal organ including vasculature so that at least a portion of cells contained therein resume biological activity; and (e) introducing at least one whole gonadal organ including vasculature into the patient so that a blood vessel present in the gonadal organ is supplied with blood by a vasculature system belonging to the patient.

According to yet another aspect of the present invention there is provided a method of assuring a supply of viable gametes for future use. The method includes; (a) removing at least one whole gonadal organ including vasculature from a patient; (b) cryo-preserving the at least one whole gonadal organ including vasculature; (c) waiting until viable gametes are desired by the patient; (d) thawing the gonadal organ so that at least a portion of cells contained therein resume biological activity; and (e) introducing the at least one whole gonadal organ including vasculature the patient so that the at least one whole gonadal organ including vasculature is supplied with blood by a vasculature system belonging to the recipient.

According to further features in preferred embodiments of the invention described below, a single individual serves as both the donor and the recipient.

According to still further features in the described preferred embodiments the whole organ including vasculature has a capacity to fulfill at least one function selected from the group consisting of oogenesis, spermatogenesis, supply of a hormone, supply of a growth factor, metabolism of a precursor into an end-product, elimination of waste and regulation of a physiologic process.

According to still further features in the described preferred embodiments the method further includes facilitating angiogenesis of the whole organ including vasculature.

According to still further features in the described preferred embodiments the organ is a gonadal organ selected from the group consisting of an ovary and a testicle.

According to still further features in the described preferred embodiments the period of time is selected from the group consisting of: (i) sufficient time for resolution of an acute medical condition of the donor; (ii) sufficient time for a change in a physiologic state of the recipient; (iii) sufficient time for identifying a recipient unlikely to reject tissue from the donor.

According to still further features in the described preferred embodiments the single individual is a cancer patient attempting to avoid sterility.

According to still further features in the described preferred embodiments the single individual is a woman wishing to alleviate menopausal symptoms by implantation of a previously removed ovary including vasculature after onset of menopause.

According to still further features in the described preferred embodiments the single individual is a woman wishing to achieve altered fertility status by implantation of a previously removed whole ovary including vasculature.

According to still further features in the described preferred the at least one whole gonadal organ including vasculature is selected from the group consisting of an ovary and a testicle.

According to still further features in the described preferred embodiments the method of further includes installing at least one prosthetic testicle in a scrotum of the patient. According to still further features in the described preferred embodiments the method of further includes administering sex hormones to the patient.

The present invention successfully addresses the shortcomings of the presently known configurations by providing methods of preserving functionality of an organ, preserving fertility of a patient undergoing a treatment expected to cause sterility and assuring a supply of viable gametes for future use.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of methods of preserving functionality of an organ, preserving fertility of a patient undergoing a treatment expected to cause sterility and assuring a supply of viable gametes for future use which can be used to remove an organ, cryopreserve the removed organ and reintrodue the cryopreserved organ into a recipient.

Specifically, the present invention assures that the vasculature of the recipient supplies blood to the introduced organ or a portion thereof.

Figure 1:
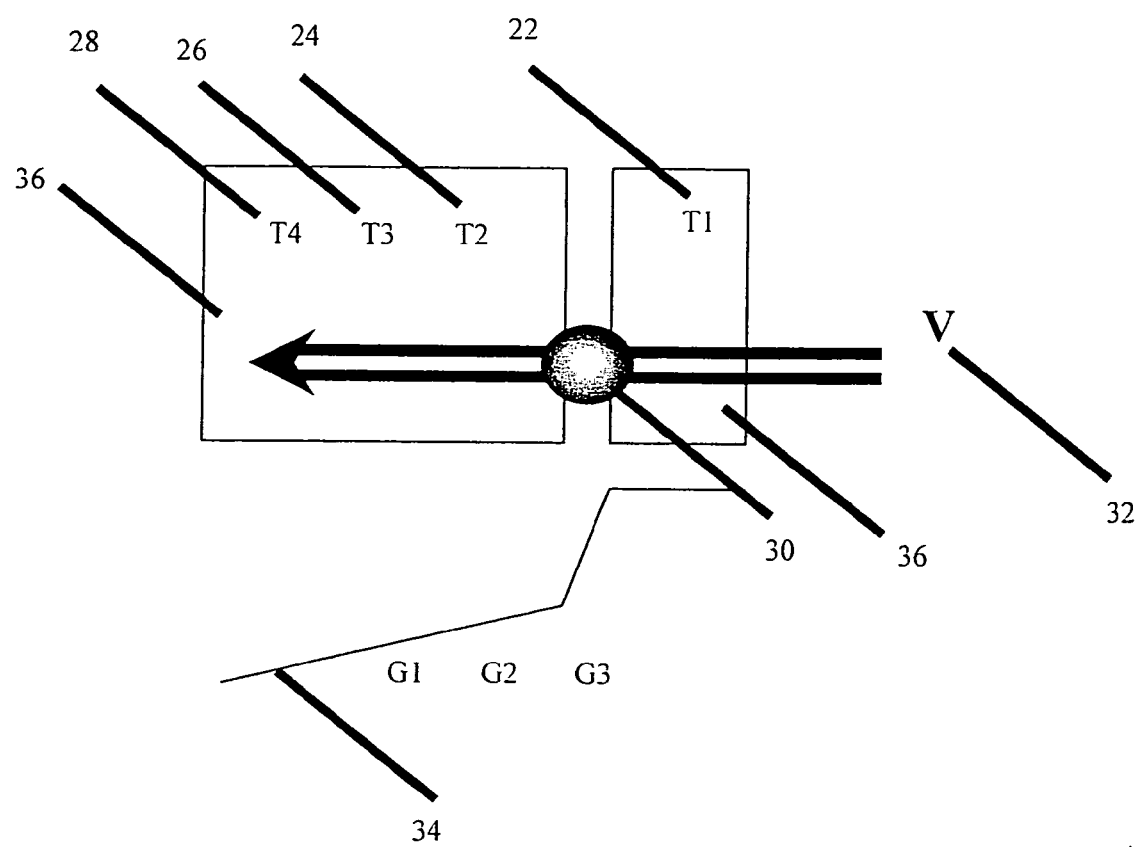
FIG. 1 is a diagram of a device used for freezing of a whole organ suitable for use in the context of the present invention.

For purposes of better understanding the present invention, as illustrated in FIGS. 1-4 of the drawings, reference is first made to the construction and operation of a conventional (i.e., prior art) thermal gradient device as illustrated in FIG. 1.

A freezing device 20 (multi-Gradient-Directional (MGD) IMT technologies; Israel) according to earlier teachings of Arav (U.S. Pat. No. 5,873,254) was employed to freeze removed whole organs. In brief, device 20 includes a plurality of temperature domains (e.g. 22, 24, 26 and 28) within 270 mm cooper blocks 36. A tube containing a whole organ 30 is pushed at a constant velocity (V; 32) through the predetermined temperature gradient (34; G=ΔT/d where ΔT is temperature differences and d is the distance between temperatures) resulting in a cooling rate (B) according to the equation B=G*V. The cooling rate may be set to, for example, 0.03° C./min by varying velocity 32 at which tube 30 containing the organ passes through the gradient 34. Seeding is typically performed at the tip of the tube 30 and ice interphase is propagated according to the freezing point of the solution.

The principles and operation of methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 2:
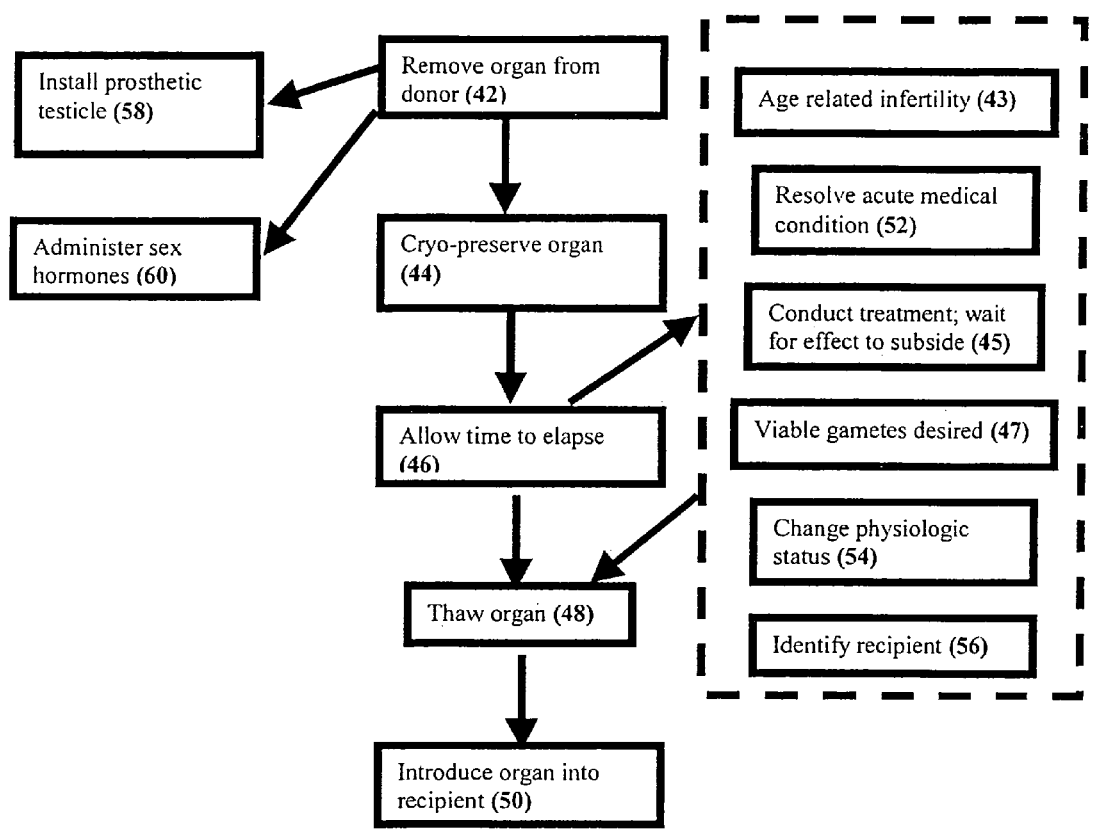
FIG. 2 is a flow diagram illustrating essential steps in methods according to the present invention.
Figure 3:
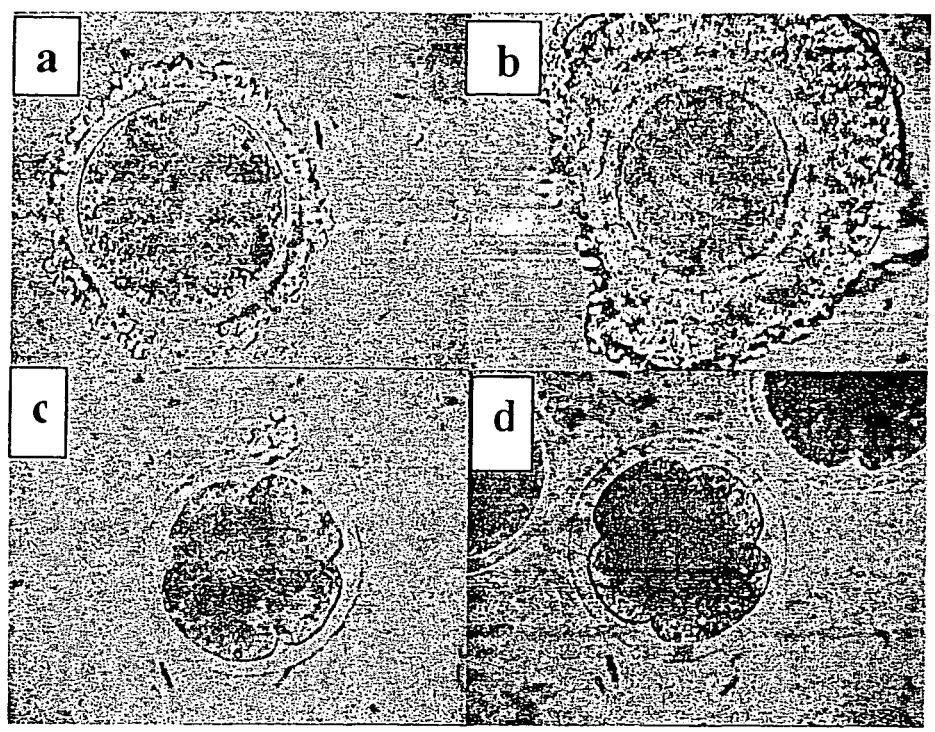
FIGS. 3*a-d* are photomicrographs of oocytes (panels a and b) and enbryos (panels c and d) from experimental (panels a and c) and control (panels b and d) ovaries.
Figure 4:
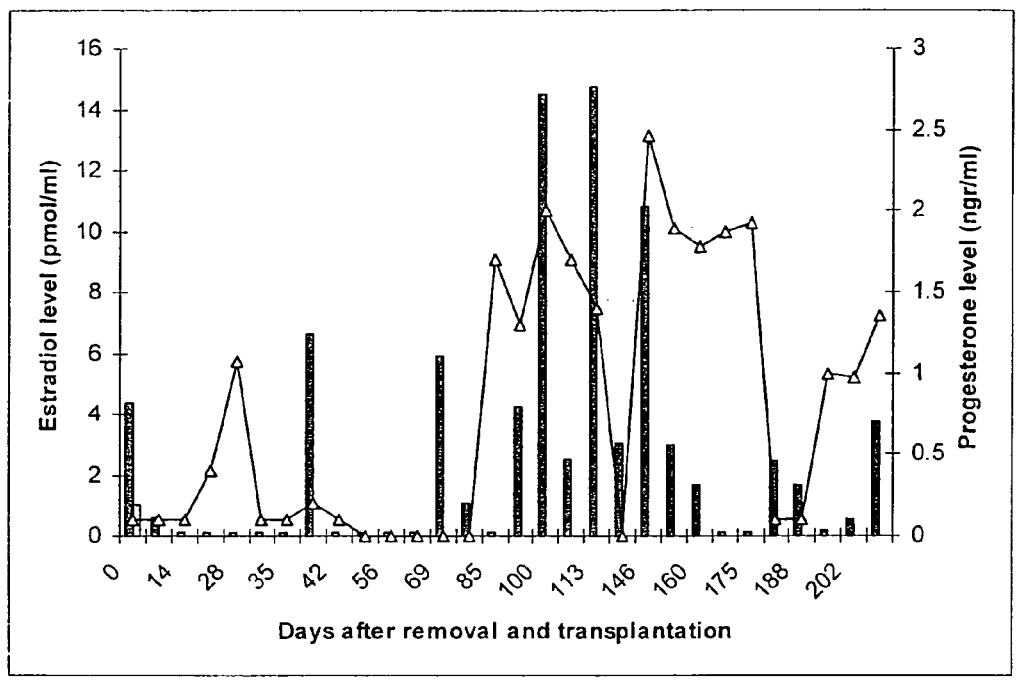
FIG. 4 is a graph illustrating estradiol and progesterone levels as a function of time post transplantation.

Referring now to the drawings, FIG. 2 illustrates a method 40 of preserving functionality of an organ. Method 40 includes removing 42 at least a whole organ including vasculature from a donor. Method 40 further includes cryo-preserving 44 the whole organ including vasculature and allowing 46 a period of time to elapse. Method 40 further includes thawing 48 the whole organ including vasculature so that at least a portion of cells contained therein resume biological activity. Method 40 further includes introducing 50 the whole organ including vasculature into a recipient so that a blood vessel present in the vasculature of the whole organ including vasculature is supplied with blood by a vasculature system belonging to the recipient. Preferably, a single individual serves as both the donor and the recipient. The single individual may be, for example, a cancer patient attempting to avoid sterility. Alternately, the single individual may be a woman wishing to alleviate menopausal symptoms by implantation of a previously removed ovary including vasculature after onset of menopause. Alternately, but also preferably, the single individual is a woman wishing to achieve altered fertility status by implantation of a at least one previously removed whole ovary including vasculature. In this case, a woman may elect to have one or both ovaries remove when she is relatively young, and then have one or both ovaries re-implanted at a later time when she wishes to conceive.

According to various preferred embodiments of method 40, the whole organ including vasculature may be introduced to fulfill at least one function including, but not limited to, oogenesis, spermatogenesis, supply of a hormone, supply of a growth factor, metabolism of a precursor into an end-product, elimination of waste or regulation of a physiologic process. Most preferably, the organ is a gonadal organ i.e. an ovary or a testicle.

Preferably, method 40 further includes facilitating angiogenesis of the whole organ including vasculature.

Allowing a period of time to elapse may be for a variety of reasons, such as, for example, allowing sufficient time for resolution 52 of an acute medical condition of the donor, or allowing sufficient time for a change 54 in a physiologic state of the recipient, or allowing sufficient time for identifying 56 a recipient unlikely to reject tissue from the donor.

The invention is further embodied by method 40 of preserving fertility of a patient undergoing a treatment expected to cause sterility. Method 40 includes removing 42 at least one whole gonadal organ including vasculature from the patient. Method 40 further includes cryo-preserving 44 the at least one whole gonadal organ including vasculature. Method 40 further includes conducting 45 the treatment and waiting for an effect thereof to subside. Method 40 further includes thawing 48 the at least one whole gonadal organ including vasculature so that at least a portion of cells contained therein resume biological activity; and introducing 50 the at least one whole gonadal organ including vasculature into the patient so that a blood vessel present in the gonadal organ is supplied with blood by a vasculature system belonging to the patient. The at least one whole gonadal organ including vasculature is either an ovary or a testicle depending upon the sex of the patient.

In cases where the gonadal organ is a testicle, method 40 preferably further includes installing 58 at least one prosthetic testicle in a scrotum of the patient. This step is performed to prevent damage to the patient's self image.

Whether the patient is male or female, method 40 further includes administering 60 sex hormones to the patient if both gonadal organs are removed so that secondary sex characteristics are not affected.

The present invention is further embodied by method 40 of assuring a supply of viable gametes for future use. Method 40 includes removing 42 at least one whole gonadal organ including vasculature from a patient. Cryo-preserving 44 the at least one whole gonadal organ including vasculature and waiting until viable gametes are desired 47 by the patient. Method 40 further includes thawing 48 the gonadal organ so that at least a portion of cells contained therein resume biological activity and introducing 50 the at least one whole gonadal organ including vasculature into the patient so that the at least one whole gonadal organ including vasculature is supplied with blood by a vasculature system belonging to the recipient.

Freezing of whole organs in conjunction with methods 40 may be accomplished, for example, using devices taught by Arav (U.S. Pat. No. 5,873,254) for example by placing the whole organ in a volume of freezing solution; pushing the solid tissue at a velocity (V) through a predetermined temperature gradient (G) thus determining a cooling rate (B) according to the equation B=G*V; initiating crystallization at a predetermined position within the temperature gradient (G); and allowing the solid tissue to continue to move through the temperature gradient (G) at the velocity. According to Arav G=ΔT/d where ΔT is the temperature difference and d is the distance over which it is maintained. Thawing of the cryo=preserved organ may be accomplished, for example, by placing the cryopreserved organ into a 66° C. environment for a first period of tim and placing the cryopreserved solid tissue into a 38° C. water bath for a second period of time as described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Animal Cell Culture" Freshney. R. I., ed. (1986); "Methods in Enzymology" Vol. 1-317, Academic Press; "PCR Protocols: A Guide To Methods And Applications", Academic Press, San Diego, Calif. (1990); all of which are incorpotaed by reference as if fully set forth herein. Other general references are provided throughout this document. The procedures therein are believed to be well known in the art and are provided for the convenience of the reader. All the information contained therein is incorporated herein by reference.

Materials and Methods

Reference is first made to the following materials and methods which are generally employed in performing experiments described in examples set forth hereinbelow.

Cryopreservation of Organs:

Organs (e.g. ovaries) were removed from donor animals and perfused with Belzer UW solution (ViaSpan®, Do Pont Pharma, USA) +10% dimethyl sulfoxide (DMSO; Sigma Chemicals, St. Louis, USA) by insertion of a catheter into a blood vessel of the organ.

Organs, and their vasculature network, were then transferred to 16×100 mm glass tubes (Manara, Israel) and frozen using a commercially available (IMT, Israel) multi-gradient directional freezing apparatus (described in U.S. Pat. No. 5,873,254). Different freezing temperatures were assayed as described hereinbelow.

Cryo-Preservation Apparatus:

A Cryopreservation apparatus as described by Arav (U.S. Pat. No. 5,873,254; FIG. 1) was employed for freezing the ovaries as described hereinabove. Briefly, the apparatus includes 4 temperature domains within 270 mm copper blocks. A test tube containing the sample is pushed at a constant velocity (V) through the predetermined temperature gradient (G=ΔT/d where ΔT is temperature differences and d is the distance between temperatures) resulting in a cooling rate (B) according to the equation B=G*V. The cooling rate was set to 0.1° C./min by varying the speed the tube passes through the temperature gradient. Seeding was performed at the tip of the test tube and ice interphase was propagated according to the freezing point of the solution.

In-Vitro Follicular Assays:

Follicles were aspirated using a 22 gauge needle connected to a 5 ml syringe and thin ovarian cortex slices were cut. The granulose cells and follicular viability was assessed using FDA (fluorescein diacetate)/DAPI (4,6-diainidino-2-phenylindole) fluorescent live/dead staining (Molecular Probes, Leiden, the Netherlands and Merk, Germany).

Thawing of Cryopreserved Organs:

Organs were first immersed in a high temperature (66-68° C.) water bath for 10 to 20 seconds followed by immersion in a 38-40° C. water bath for 10 to 120 seconds. Ovaries were then perfused with 0.5M sucrose and 150 iu heparin to remove cryoprotectants and prevent blood clotting.

Introduction of Organs into Recipients:

Transplantation was performed by re-anastomizing arteries and veins of the transplanted organ with 10 zero sutures (Ethilon; Johnson and Johnson, U.S.A.). Success of the procedure was evaluated by observing arterial blood pulse and venous return flow in the newly introduced organ. A hyaluronic acid gel was employed to prevent adhesions (Intergel; Johnson and Johnson, U.S.A.). For ovary transplantation was autologus.

Fertility Evaluation of Transplanted Ovaries:

Two months after transplantation, 600 iu of PMSG were administered to the recipient to cause superovulation (Intervet International BV; Boxmeer, Netherlands). Three days later follicles were aspirated from the transplanted organ using a syringe and a 20 gauge needle. Oocytes were transported in a mobile incubator (Minitube, Germany) at 38° C. in buffer medium to an IVF laboratory. Aspirated oocytes were then put into TCM-199 maturation medium supplemented with 10% (V/V) heat-inactivated fetal calf serum (FCS) (Biolab, Jerusalem, Israel), 0.2 mmol Na pyruvate $l^{-1}$, 5 μg gentamicin $l^{-1}$, 10 μg ovine LH $ml^{-1}$ (NIADDK-NIH-26, AFP5551B, Bethesda, Md.), 1 μg ovine FSH $ml^{-1}$ (NIADDK-NIH-20, AFP7028D, Bethesda, Md.) and 1 μg estradiol $ml^{-1}$ and incubated in a 38.5° C. in a humidified atmosphere of 5% $CO_2$ in air. After maturation, oocytes were denuded from cumulus cells in the maturation wells and placed for 5 min. in the ionomycin medium: 10 ml TCM-199, supplemented with 10% (V/V) heat-inactivated FCS, 0.2 mmol Na pyruvate $l^{-1}$, 5 μg gentamicin $l^{-1}$, and 5 μmol of ionomycin $l^{-1}$. Oocytes were transferred to 6-dimethylami-nopurine (6-DMAP) medium (10 ml of TCM 199 supplemented with 2 mmol of 6-DMAP $l^{-1}$) for 4.5 h. The oocytes were then washed three times in a cleavage medium (Sydney IVF Cleavage Medium, Cook, Australia) and transferred into 50 μl cleavage drops under mineral oil for another three days. Cleaved embryos were counted on day 4 (activation day=0) and transferred to 50 μl drops under mineral oil of blastocysts medium (Sydney IVF Blastocyst Medium, Cook, Australia). Blastocysts were counted after 8-10 days.

Hormonal Status:

Progesterone and estradiol levels were analyzed in serum samples bi-weekly. Progesterone was measured using COAT-A-COUNT Progesterone DPC®, USA. Estradiol levels were measured by ESTER-US-CT, ORIS Group, France.

Example 1

In Vitro Assay of Viability of Sheep Ovaries After Thawing

In order to determine the effect of freezing temperature on subsequent viability, fifteen Assaf sheep ovaries were collected 10 min after slaughter. The ovaries were perfused with a Belzer UW solution (ViaSpan®, Do Pont Pharma, USA)+ 10% DMSO (Sigma, St. Lois, USA) for 3 min, in order to obtain maximal permeability of the organ to DMSO. After perfusion, the ovaries were loaded into 16×100 mm glass test tubes (Manara, Israel) in UW+10% DMSO and transferred to the freezing apparatus (IMT, Israel) described hereinabove. Control ovaries were perfused as above but were not cryopreserved. Ovaries were frozen to different temperatures as detailed in table 1.

TABLE 1

Freezing parameters of whole ovine ovaries

| EXP. | T1 | T2 | T3 | T4 | T5 | V | CR |
|---|---|---|---|---|---|---|---|
| 1 | 0° C. | −6° C. | −10° C. | −14° C. | — | 0.03 mm/s | 0.1° C./min |
| 2 | 0° C. | −6° C. | −18° C. | −30° C. | — | 0.01 mm/s | 0.1° C./min |
| 3 | 0° C. | −6° C. | −18° C. | −30° C. | −196° C. | 0.01 mm/s | 0.1° C./min |

Briefly, the cooling rate was set to 0.1° C./min by varying the speed of the tube through the temperature gradient. Seeding was performed at the tip of the test tube and ice interface was propagated according to the freezing point of the solution. 15 minutes after reaching the final temperature the test tube was thawed. When −196° C. was used as the final temperature, ovaries were stored in LN for 2 days to one week before being thawed.

Frozen ovaries were thawed as described hereinabove. The frozen-thawed whole ovaries were then washed in buffer medium at 38° C. Follicles were aspirated with a 22 G needle connected to a 5 ml syringe in order to obtain granulosa cells. Thin slices were cut from the ovarian cortex. The granulose cells and primordial and small antral follicules were evaluated for viability using fluorescent microscopy as described by Oktay et al. (Fertil. and Steril. 1997(67):481-486) FDA (fluorescein diacetate)/DAPI (4,6-diamidino-2-phenylindole) fluorescent live/dead staining (Molecular Probes, Leiden, the Netherlands and Merk, Germany) was performed.

Granulosa cells that were evaluated after freezing and thawing showed no statistically significant differences from controls (Table 2). The survival of small follicles (small antral and primordial follicules) showed no statistically significant differences from controls (Table 2). Means were calculated using the General Linear Model procedure of JMP (SAS Institute, 1994) and differences between treatments examined by analysis of variance. Significance was P<0.05.

These results clearly demonstrate that small follicles and granulose cells are not damaged by freezing and thawing using conditions described herein.

TABLE 2

In vitro study survival of ovaries after freezing to different temperatures

| Exp. | Number of ovaries | Storage temp. | Viability of granulosa cells(±SE) | Live follicles/dead follicles |
|---|---|---|---|---|
| Cont. | 3 | Room temp. | 50% ± 7 | 101/105 |
| 1 | 3 | −14° C. | 38% ± 29 | 69/69 |
| 2 | 3 | −30° C. | 40% ± 16 | 18/37 |
| 3 | 5 | −196° C. | 58 ± 16 | 68/73 |

Example 2

In Vivo Assay of Viability Sheep Ovaries After Thawing

In order to verify the results of Example 1 in an in vivo system, eleven-month-old Assaf sheep were subjected to oophorectomy under general anaesthesia via longitudinal laparotomy. The uterus and ovaries were exposed and a dissection of the right ovarian artery and vein was performed. The ovary was perfused in vivo with UW+10% DMSO for 3 min. It was then excised and inserted into a freezing tube containing UW+10% DMSO. Slow freezing was performed by cooling from 0 to −6° C. over 2 min, seeding was done before entering −6° C. and cooling to −14° C., −30° C. and thawing after 15 minutes or to −30° C. and then direct plunging into LN and then thawing. The cooling rate of the three different procedures was 0.1° C./min. After 15 min at the final temperature thawing was performed by plunging the test tube into a 66° C. water bath for 20 s and then into a 40° C. water bath for 2 min. Ovarian vascular transplantation was performed by re-anastomosing the ovarian artery and vein with 10 zero sutures (Ethilon, Johnson and Johnson). After the arterial anastomosis was completed, blood flow was verified by observing blood pulse in the ovary and venous return through the ovarian vein.

Two months after autotransplantation, 600 iu PMSG (intervet international BV, Boxmeer-Holand, France: intervet SA 49100-Angers, Pais-Bas) was administered. Oocytes were aspirated three days later, matured, and parthanogenetically activated in vitro as described hereinabove.

Parthenogenetic activation resulted in normal development of ⅗ retrieved oocytes, pictures of oocytes (FIGS. 3a and b) and embryos (FIG. 3c and) indicate no apparent difference between experimental (FIGS. 3a and c) and control (FIGS. 3b and d) oocytes or embryos. Following oophorectomy of the unfrozen contralateral ovary in the recipient, blood was taken bi-weekly for two months and progesterone and estradiol levels were evaluated using a commercially available assay (Coat-A-Count Progesterone, DPC, LA, USA and ESTR-US-CT, ORIS Group, France) Results are summarized in FIG. 4.

Briefly, estrogen and progesterone levels dropped to negligible levels immediately post transplantation. Estrogen levels surged four weeks following transplantation of an ovary frozen in liquid nitrogen. Cyclical estrogen and progesterone thereafter were measured for over thirty weeks. These results clearly demonstrate that the implanted ovary restored normal hormonal balance to the recipient. Further, normal oocyte division and development (FIG. 3) indicate that the primordial and small antral follicles in the transplanted ovary recover from freezing without ill effect. In summary, these results indicate that it is now feasible to remove and freeze a solid organ for subsequent transplantation into a recipient and to achieve full physiologic activity from the thawed transplanted organ. This capacity is expected to find utility in a variety of clinical contexts as detailked hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Dietzmang R. H., Robelo, A. E., Graham, E. F., Crabo, B. G. & Lillehei, R. C. Long term functional success following freezing of canine kidneys. *Surgery* 74, 181-189 (1974).
2. Guttman, E. M., Lizin, J., Robitaille, P., Blanchard, H. & Turgeon-Knaack, C. Survival of canine kidneys after treatment with dimethyl sulphoxide, freezing at −80° C. *Cryobiology* 14, 559-567 (1977).
3. Karow, A. M. Jr. In Organ preservation for transplantation. (ed. Karow, A. M. and Pegg, D. E.) 517-552 (Marcel Dekker, New-York, US, 1981).
4. Jacobsen, I. A., Pegg, D. E., Starklut, H., Chemnitz, C., Hunt, C., Barfort, P. & Diaper, M. Effect of cooling and warming rate on glycerolized rabbit kidneys. *Cryobiology* 19, 668 (1982).
5. Schmid, W. D., Survival of frogs in low temperature. *Science* 215, 5 (1982).
6. Storey, K. B. Storey, J. M., Brooks, S. P., Churchill, T. A. & Brooks, R. J. Hatchling turtles survive freezing during winter hibernation *Proc. Natl. Acad. Sci. USA* 85(21), 8350-8354 (1988).
7. Storey, K. B. Life in a frozen state: Adaptive strategies for natural freeze tolerance in amphibians and reptiles. *Am. J. Physiol.* 258, R559 (1990).
8. Wang, T., Banker, M. C., Clydon, M., Hicks, G. L. & Layne, J. R. Freezing preservation of mammalian cardiac explant V. Cryoprotection by ethanol. *Cryobiology* 29, 470-477 (1992).
9. Banker, M. C., Layne, J. R., Jr. Hicks, G. L., Jr. & Wang, T. Freezing preservation of mammalian cardiac explant. IV. Functional recovery after 8-hours freezing. *Curr. Surg.* 48, 428-430 (1991).
10. Rubinsky, B., Arav, A., Hong, J. S. & Lee, C. Y, Freezing of mammalian livers with glycerol and antifreeze proteins. Bioch. *Bioph. Res. Comm.* 200, 2, 732-741 (1994).
11. Soltys, K. A., Batta, A. K. & Baburao, K. Successful nonfreezing, subzero preservation of rat liver with 2,3-Butanediol and type I antifreeze protein. *J. of Surgical Research* 96, 30-34 (2001).
12. Karlasson, J. O. M. & Toner, M. Long term storage of tissues by cryopreservation. *Critical issues Biomaterials* 17, 243-256 (1996).
13. Mazur, P. The role of intracellular freezing in the death of cells cooled at supraoptimal rates. *Cryobiology* 14, 251-272 (1977).
14. Fuller, B. J. In the effect of low temperature on biological systems, (ed. Grout B. W. W. & Morris G. J.) 432-450 (Edward Arnold, London, GB, 1987).
15. Pegg, D. E. In The biophysic of organ cryopreservation (ed. Pegg, D. E. & Karow, A. M. Jr) 117 (Plenum, Press, New York, US, 1987).
16. Fahy, G. M. Macfarlane, D. R., Angell, C. A. & Meryman, H. T. Vitrification as an approach to cryopreservation. *Cryobiology* 21, 407-426 (1984).
17. Kheirabadi, B. S. & Fahy, G. M. Permanent life support by kidneys perfused with a vitrifiable (7.5 molar) cryoprotectant solution. *Transplantation* 70(1), 51-57 (2000).
18. Steponkus et al. Cryopreservation of *Drosophila melanogaster* embryos. *Nature* 345, 168-169 (1990).
19. Mazur, P., Cole, K. W., Hall, J. W., Schreuders, P. D. & Mahowald, A. P. Cryobiological preservation of *Drosophila* embryos. *Science* 258, 1932-1935 (1992).
20. Armitage, W. J. & Juss, B. K. The influence of cooling rate on survival of frozen cells differs in monolayer and in suspensions. *Cryoletter* 17, 213-218 (1996).
21. Koebe, H. G. Werner, A., Lange. V. & Schildberg, F. W. Temperature gradients in freezing chambers of rate-controlled cooling machines. *Cryobiology* 30, 349-353 (1993).
22. Arav, A. Device and methods for multigradient directional cooling and warming of biological samples. U.S. Pat. No. 5,873,254 (1999).
23. Byrne, J., Mulvihill, J. J. & Myers, M. H. Effects of treatment on fertility in long-term survivors of childhood or adolescent cancer. *N Engl J Med.* 317, 1315-21 (1987).
24. Ataya, K. and Moghissi, K. Chemotherapy-induced premature ovarian failure: mechanisms and prevention. *Steroids.* 54, 607-626 (1989).
25. Familiari, G. et al. Ultrastructure of human ovarian primordial follicles after combination chemotherapy for Hodgkin's disease. *Hum Reprod.* 8, 2080-2087 (1993).
26. Arav, A. et al Phase transition temperature and chilling sensitivity of bovine oocytes *Cryobiology* 33, 589-599 (1996).

27. Zeron, Y., Pearl, M., Borochov, A., & Arav, A. Kinetic and temporal factors influence chilling injury to germinal vesicle and mature bovine oocytes. *Cryobiology* 38, 35-42 (1999).

28. Zenzes, M. T., Bielecki, R., Casper, R. F. & Leibo S. P. Effects of chilling to 0 degrees C. on the morphology of meiotic spindles in human metaphase II oocytes. *Fertil. Steril.* 75, 769-777 (2001).

29. Hovatta, O. et al. Cryopreservation of human ovarian tissue using dimethylsulphoxide and propanediol-sucrose as cryoprotectants. *Hum. Reprod.* 11, 1268-1272 (1996).

30. Newton, H., Aubard, Y., Rutherford, A., Sharma, V. & Gosden, R. Low temperature storage and grafting of human ovarian tissue. *Hum. Reprod.* 11, 1487-1491 (1996).

31. Gosden, R. G. Low temperature storage and grafting of human ovarian tissue. *Mol. Cell Endocrinol.* 163, 125-129 (2000).

32. Gosden, R. G., Baird, D. T., Wade, J. C. & Webb, R. Restoration of fertility to oophorectomized sheep by ovarian autografts stored at −196 degrees C. *Hum. Reprod.* 9, 597-603 (1994).

33. Baird, D. T., Webb, R., Campbell, B. K., Harkness, L. M. & Gosden, R. G. Long-term ovarian function in sheep after ovariectomy and transplantation of autografts stored at −196 C. *Endocrinology* 140, 462-471 (1999).

34. Kim, S. S., Battaglia, D. E. & Soules, M. R., The future of human ovarian cryopreservation and transplantation: fertility and beyond *Fert. And Sterl.* 75, 6 (2001).

35. Siebzehnrubl, E., Kohl, J., Dittrich, R. & Wildt, L. Freezing of human ovarian tissue—not the oocytes but the granulosa is the problem. *Mol. Cell Endocrinol.* 27, 169(1-2), 109-111(2000).

36. Redford, J. A. et al. Orthotopic reimplantation of cryopreserved ovarian cortical strips after high-dose chemotherapy for Hodgkin's lymphoma. *Lancet* 357, 1172-1175 (2001)

What is claimed is:

1. A method of preserving a whole human ovary, comprising:
    a. freezing the whole human ovary including vasculature, by perfusing the ovary including vasculature with a solution comprising a cryoprotectant and placing the ovary in a solution comprising a cryoprotectant; moving the ovary through a predetermined temperature gradient, thereby creating a cooling rate in a range of from 0.03 to 1.5° C./minute; seeding the solution to propagate an ice interphase according to the freezing point of the solution; and storing the ovary including vasculature at a temperature below freezing temperature; and
    b. thawing the whole human ovary including vasculature, and removing the solution comprising a cryoprotectant, to obtain a thawed whole human ovary, such that after thawing at least a portion of cells contained therein resume biological activity and a blood vessel present in the vasculature is in a state to permit its supply with blood by a vasculature belonging to an ovary recipient, wherein the thawed whole human ovary including vasculature is suitable for transplantation and re-anastomosis in the ovary recipient.

2. The method of claim 1, wherein the cooling rate is 0.03° C./minute.

3. The method of claim 1, wherein the cooling rate is 0.1° C./minute.

4. The method of claim 1, wherein said moving the ovary through a predetermined temperature gradient is at a velocity selected from the group consisting of 0.03 mm/sec. and 0.01 mm/sec.

5. The method of claim 1, wherein after thawing the whole human ovary has a capacity to fulfill at least one function selected from the group consisting of oogenesis, supply of a hormone, and metabolism of a precursor into an end product.

6. The method of claim 1, wherein thawing comprises a first sub-step of warming the frozen whole human ovary at a first temperature of between 66° C.-68° C. followed by a second sub-step of warming the whole human ovary at a second temperature of between 38° C.-40° C.

7. The method of claim 1, wherein the at least portion of cells contained are capable of resuming biological activity after a storage period between 2 days and one week, and wherein the storage is in liquid nitrogen.

8. The method according to claim 1, wherein the cooling rate is in a range of from 0.03° C./min to 0.1° C./min and said moving the ovary through a predetermined temperature gradient is at a velocity in a range of from 0.03 mm/sec to 0.01 mm/sec.

9. The method according to claim 1, further comprising transplanting and re-anastomising the thawed whole human ovary in the ovary recipient such that the ovary is supplied with blood by the vasculature system of the ovary recipient.

10. The method of claim 1, wherein said human ovary is about the size of an adult sheep ovary.

11. A method of preserving a whole human ovary, comprising:
    a. freezing the whole human ovary including vasculature, by perfusing the ovary including vasculature with a solution comprising a cryoprotectant and placing the ovary in a solution comprising a cryoprotectant; moving the ovary through a predetermined temperature gradient, thereby creating a cooling rate in a range of from 0.03 to 1.5° C./minute; and seeding the solution to propagate an ice interphase according to the freezing point of the solution; and
    b. storing the whole human ovary at a temperature of in a range of −14° C. to −196° C.;
    wherein upon subsequent thawing and removal of the solution comprising a cryoprotectant, at least a portion of the cells contained in the whole human ovary resume biological activity upon thawing, and a blood vessel present in the vasculature is in a state to permit its supply with blood by a vasculature belonging to an ovary recipient, and
    wherein when thawed, the whole human ovary including vasculature is suitable for transplantation and re-anastomosis in the ovary recipient.

12. The method of claim 11, wherein the temperature gradient terminates at −30° C., and wherein after moving the whole human ovary along the gradient, the whole human ovary is placed directly in liquid nitrogen.

13. The method of claim 11, wherein the at least portion of cells contained are capable of resuming biological activity after a storage period between 2 days and one week, and wherein the storage is in liquid nitrogen.

14. The method of claim 11, wherein after thawing the whole human ovary has a capacity to fulfill at least one function selected from the group consisting of oogenesis, supply of a hormone, and metabolism of a precursor into an end product.

15. A method of preserving a whole human ovary, comprising:

a. freezing the whole human ovary, by perfusing the ovary including vasculature with a solution comprising a cryoprotectant and placing the ovary in a solution comprising a cryoprotectant; moving the ovary through a predetermined temperature gradient, thereby creating a cooling rate in a range of from 0.03 to 1.5° C./minute; seeding the solution to propagate an ice interphase according to the freezing point of the solution; and storing the ovary including vasculature at a temperature below freezing temperature; and b. thawing the whole human ovary, and removing the solution comprising a cryoprotectant, to obtain a thawed whole human ovary, such that after said thawing at least a portion of cells contained therein resume biological activity, wherein a ratio of live ovarian follicles to dead ovarian follicles in said thawed whole human ovary is at least 18/37.

16. The method of claim 15, the cooling rate is in a range of from 0.03° C./min to 0.1° C./min.

* * * * *